United States Patent [19]
Van Driel et al.

[11] Patent Number: 5,756,940
[45] Date of Patent: May 26, 1998

[54] WEIGHT MEASUREMENT OF BLOOD VOLUME SOFT-SHELL VENOUS RESERVOIRS

[75] Inventors: Michael R. Van Driel, Fountain Valley, Calif.; Darren S. Gray, Grand Junction, Colo.; Victor C. H. Lam, Honolulu, Hi.; Amy P. Noss, Westerville, Ohio; Jill E. Uyeno, Honolulu, Hi.; Yu-Tung Wong, Huntington Beach, Calif.

[73] Assignee: Medtronic, Inc., Minneapolis, Minn.

[21] Appl. No.: 840,687

[22] Filed: Apr. 29, 1997

[51] Int. Cl.⁶ .................................................. G01G 9/00
[52] U.S. Cl. ........................................ 177/245; 604/65
[58] Field of Search ........................ 177/50, 245; 604/65, 604/66, 67; 73/149, 232, 262

[56] References Cited

U.S. PATENT DOCUMENTS

| | | | |
|---|---|---|---|
| 3,698,494 | 10/1972 | Gaudin | 177/245 X |
| 4,394,862 | 7/1983 | Shim | 604/67 |
| 4,469,480 | 9/1984 | Figler et al. | 604/52 |
| 4,598,733 | 7/1986 | Kanno et al. | 128/DIG. 13 X |
| 5,010,968 | 4/1991 | Barrow | 177/245 X |
| 5,371,329 | 12/1994 | Fillaud | 177/245 |

*Primary Examiner*—Elizabeth L. Dougherty
*Attorney, Agent, or Firm*—Harry G. Weissenberger

[57] ABSTRACT

An accurate real-time volume measurement of the blood content of a soft-shell venous reservoir is obtained by computing the volume from the weight of the blood in the reservoir modified by the hematocrit of the blood.

6 Claims, 2 Drawing Sheets

WEIGHT MEASUREMENT OF BLOOD VOLUME SOFT-SHELL VENOUS RESERVOIRS

FIELD OF THE INVENTION

This invention relates to the measurement of the blood volume in a soft-shell venous reservoir of a heart-lung machine, and more particularly to a method and apparatus using variations in the weight of the reservoir to track blood volume variations.

BACKGROUND OF THE INVENTION

Heart-lung machines conventionally include a venous reservoir which receives the patient's blood at a variable rate during open-heart surgery and releases it at a substantially steady rate to the oxygenation circuit from which it is returned to the patient. In the operation of the heart-lung machine, it is important for the perfusionist to be continuously advised of the exact volume of blood in the reservoir, as this information is needed to maintain the correct diluted blood volume in the patient and to calculate the proper doses of infused drugs.

Rigid hard-shell reservoirs lend themselves well to this purpose because accurate graduations can readily be inscribed on their surface. However, because the volume of the hard-shell reservoir itself is constant, it will discharge potentially lethal air into the blood circuit of the heart-lung machine if it is allowed to become empty.

Collapsible soft-shell reservoirs (i.e. plastic bags) have the advantage of increasing and reducing their volume in accordance with the amount of blood they contain, and they consequently need no airspace that could produce emboli. On the other hand, soft-shell reservoirs, because they are always exactly filled with blood, cannot provide a visible volume indication by way of graduations.

In the past, perfusionists have estimated the blood volume in soft-shell reservoirs by the appearance of the reservoir bag, but this requires experience and is not sufficiently accurate for modern requirements. To remedy this deficiency, it has previously been proposed to position the reservoir bag between two parallel plates which are biased against the bag, and whose distance from each other is indicated by a tape measure. That system, however, is not very accurate and is awkward to observe.

SUMMARY OF THE INVENTION

The present invention fills the above-described need by suspending the soft-shell venous reservoir bag from a strain gage scale and monitoring its weight as the volume of blood in the bag increases and decreases. Because the weight of a given volume of blood varies with its dilution by saline during surgery (and, for that matter, varies from patient to patient), the present invention takes advantage of the fact that the weight of blood per unit volume is a known function of hematocrit. Hematocrit in turn is readily measurable by conventional optical sensors which are in common use in cardio-surgical environments. By electronically combining hematocrit and weight indications, a very precise digital readout of blood volume in the soft-shell reservoir can be continuously obtained, regardless of the shape of the reservoir. Furthermore, the readout in this method is unaffected by any entrapped air.

DESCRIPTION OF THE PREFERRED EMBODIMENT

Figure 1:
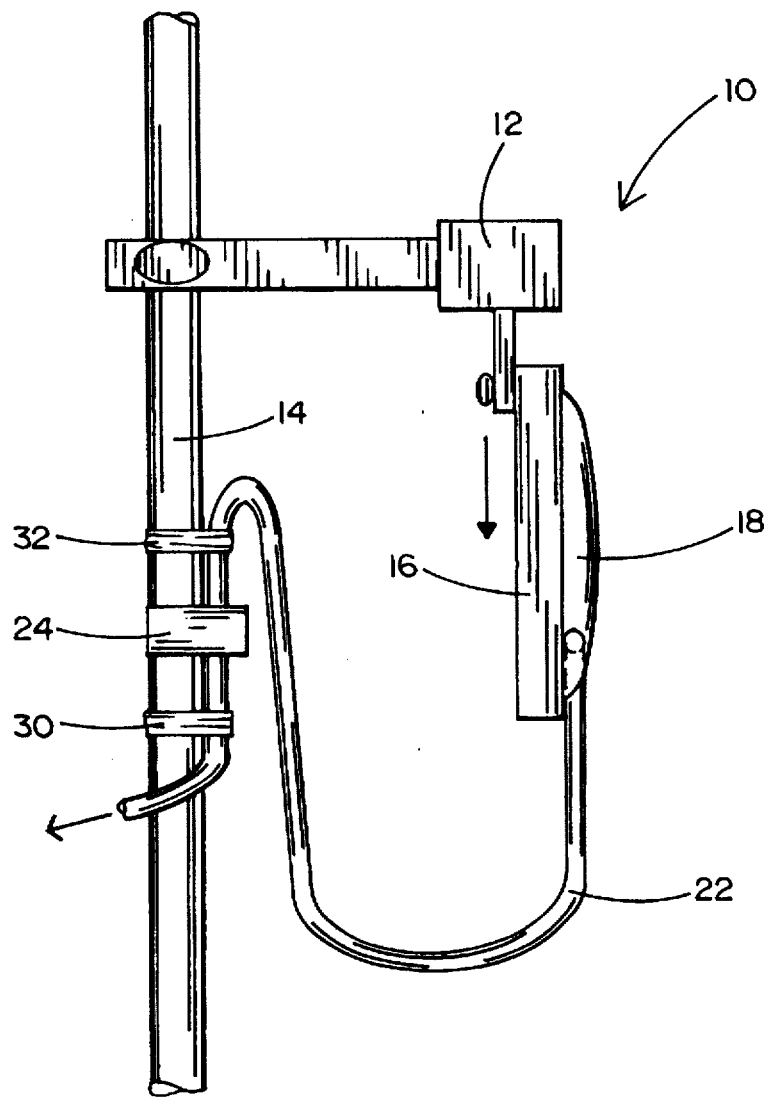
FIG. 1 is a schematic side view of the system of this invention.
Figure 2:
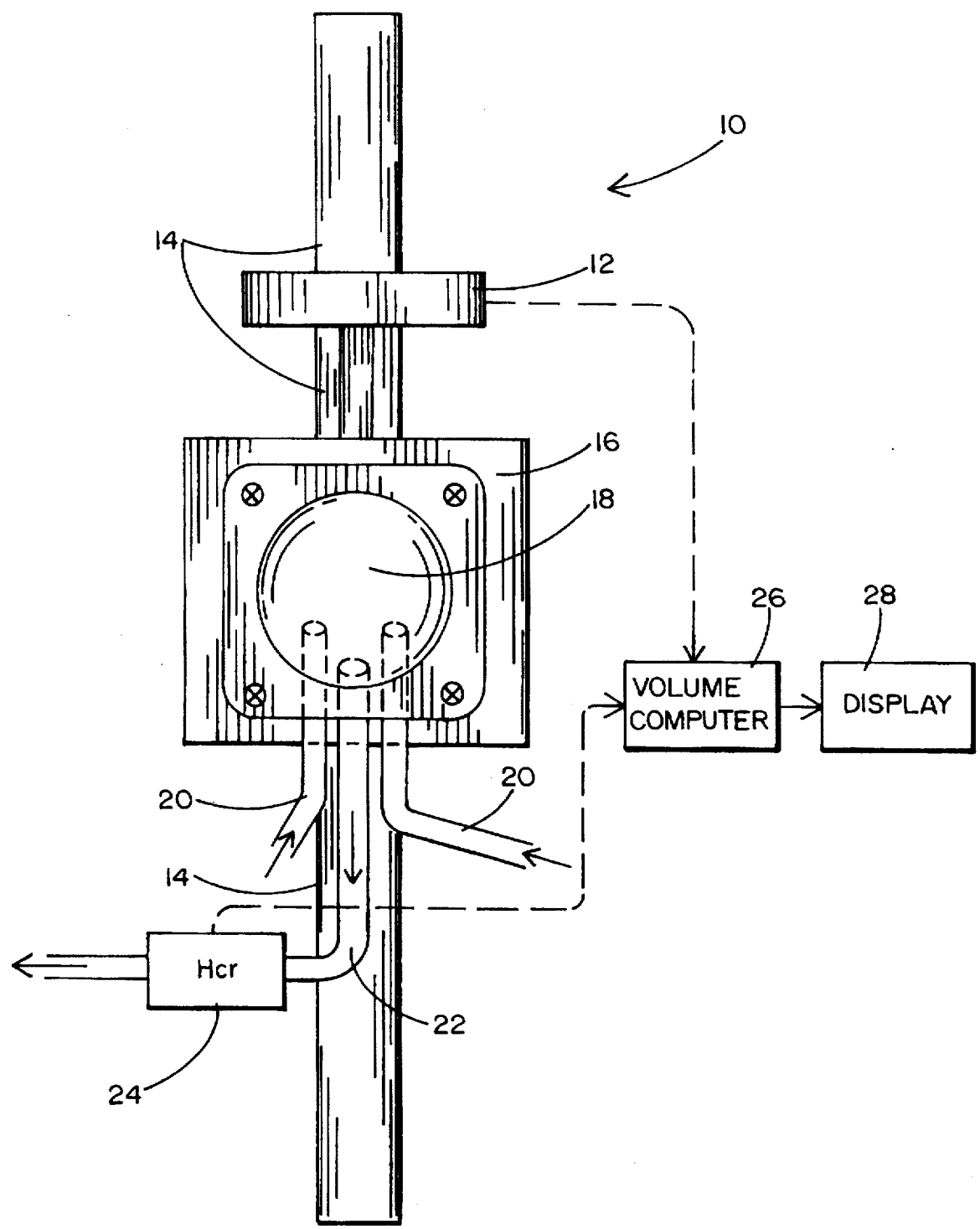
FIG. 2 is a schematic front view of the system of FIG. 1.

FIGS. 1 and 2 schematically illustrate a volume measuring system 10 according to this invention. A conventional strain gage scale providing an electronic weight indication is mounted on a conventional IV pole 14. Suspended from the scale 12 is a frame or backplate 16 which supports a soft-shell venous reservoir 18 equipped with blood inlets 20 and a blood outlet 22. The blood outlet line 22 is routed through a conventional hematocrit sensor 24 such as Medtronic, Inc.'s Biotrend sensor which produces in real time a continuous hematocrit indication of the blood flowing through line 22.

The weight indication from scale 12 and the hematocrit indication from sensor 24 are mathematically combined in accordance with the known relationship of hematocrit to blood density in a microprocessor or volume computer 26 which continuously computes blood volume.

For the purposes of this computation, hematocrit can be directly related to density. The relationship of formula (1) below has been found to be true for regular undiluted blood as well as for blood diluted with saline; the latter relationship was determined experimentally, using data on density, volume, and mass. For blood diluted with saline, the following linear relationship was obtained:

$$D = m\, Hct + b \tag{1}$$

where D is the density, Hct is the hematocrit, and m and b are constants. Using the fact that volume=mass/density, equation (1) was manipulated to equation (2)

$$V(ml) = M(g)/m/Hct + b/m \tag{2}$$

where V is the volume and M is the net mass or weight of the contents of the reservoir 18. Using experimental data, m and b were determined for formula (1) to provide $$D(g/cm^3) = 7.2 \times 10^{-4}\, Hct + 1.005 \tag{3}$$

Thus, the blood volume in the bag 18 will be $$V(ml) = M(g)/7.2 \times 10^{-4}\, Hct + 1.005 \tag{4}$$

Equation (4) yields the volume to within 1% and 0.5% for low/normal and high hematocrit readings, respectively.

The Biotrend itself measures hematocrit to within ±3 points. This translates to a ±0.2% maximum error in the predicted density. When these two errors are added in quadrature, the error is still ±1.00%. This overall error corresponds to 20 ml for 2 l of blood volume, which is ample accuracy for surgical purposes.

The blood volume computed as outlined above can readily be digitally displayed on a display 28.

The system 10 is calibrated prior to each use by filling the blood circuit and reservoir 18 with a known amount of saline solution (which has a hematocrit of zero), and setting the display 28 to indicate the known volume of saline in the reservoir 18 (i.e. the introduced volume of saline less the volume of the blood circuit lines). Then, as the saline solution is replaced by blood during surgery, changes in weight and hematocrit will increase or decrease that original reading with an accuracy more than sufficient for any surgical need.

Regarding an additional aspect of the invention illustrated in FIGS. 1 and 2, the peristaltic action of the heart-lung machine's blood pump (not shown) causes pulsating vibrations which are transmitted through the line 22 and can cause inaccuracies or fluctuations in the weight indication of scale 12. Inasmuch as this artifact is generally sinusoidal in nature, it can be eliminated by conventional electronic means, but a simpler way in accordance with this invention is to clamp the line 22 to the IV pole 14 at spaced locations by a pair of clamps 30, 32. Sufficient slack should be left in line 22 between clamp 32 and reservoir 18 to prevent any movement of reservoir 18 from significantly affecting the weight measurement of scale 12. The clamping of line 22 does not fully eliminate the vibration transmitted by the blood pump through the blood, but it damps it sufficiently to maintain a satisfactory accuracy of the volume reading.

It will be noted that unlike other methods of measuring the blood volume in a soft-shell venous reservoir, the above-described method is not subject to volume errors caused by entrapped air, because it measures the blood volume itself rather than the volume of the reservoir bag. Consequently, bleeding the air from the bag 18 is unnecessary.

It is understood that the exemplary weight measurement of blood volume in soft-shell venous reservoirs described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. A method of measuring the blood volume in a soft-shell venous reservoir, comprising the steps of:
   a) weighing said reservoir;
   b) sensing the hematocrit of the blood in said reservoir;
   c) computing the volume of blood in said reservoir as a function of weight and hematocrit; and
   d) displaying said computed volume.

2. The method of claim 1, in which said volume of blood is computed substantially as $$V(ml) = M(g)/7.2 \times 10^{-4} \, Hct + 1.005$$

wherein V is the blood volume in said reservoir, M is the net weight of the contents of said reservoir, and Hct is said hematocrit.

3. A system for measuring the blood volume in a soft-shell venous reservoir, comprising:
   a) a scale;
   b) a soft-shell blood reservoir suspended from said scale;
   c) a hematocrit sensor so positioned as to sense the hematocrit of the blood in said reservoir;
   d) said scale and sensor being arranged to produce first and second signals representative, respectively, of the net weight of the contents of said reservoir and of said hematocrit;
   e) computing apparatus receiving said first and second signals and computing therefrom an indication of the volume of blood in said reservoir; and
   f) display apparatus connected to said computing apparatus and arranged to display said computed volume.

4. The system of claim 3, in which said volume of blood is computed substantially as $$V(ml) = M(g)/7.2 \times 10^{-4} \, Hct + 1.005$$

wherein V is the blood volume in said reservoir, M is the net weight of the contents of said reservoir, and Hct is said hematocrit.

5. The system of claim 3, further comprising:
   g) an outlet conduit arranged to convey blood pumped out of said reservoir; and
   h) a fixed support, said conduit being clamped to said support, with a slack portion of said outlet conduit between the clamping point and said reservoir, so as to damp the transmission of cyclical pumping vibrations to said reservoir.

6. The system of claim 5, in which said hematocrit sensor is positioned to sense the hematocrit of blood passing through said outlet conduit.

* * * * *

US005756940C1

(12) REEXAMINATION CERTIFICATE (4609th)
United States Patent
Van Driel et al.

(10) Number: US 5,756,940 C1
(45) Certificate Issued: Jul. 2, 2002

(54) WEIGHT MEASUREMENT OF BLOOD VOLUME SOFT-SHELL VENOUS RESERVOIRS

(75) Inventors: Michael R. Van Driel, Fountain Valley, CA (US); Darren S. Gray, Grand Junction, CO (US); Victor C. H. Lam, Honolulu, HI (US); Amy P. Noss, Westerville, OH (US); Jill E. Uyeno, Honolulu, HI (US); Yu-Tung Wong, Huntington Beach, CA (US)

(73) Assignee: Medtronic, Inc., Minneapolis, MN (US)

Reexamination Request:
No. 90/005,552, Nov. 24, 1999

Reexamination Certificate for:
Patent No.: 5,756,940
Issued: May 26, 1998
Appl. No.: 08/840,687
Filed: Apr. 29, 1997

(51) Int. Cl.[7] ............................................... G01G 19/00
(52) U.S. Cl. ......................................... 177/245; 604/65
(58) Field of Search .......................... 73/149, 232, 262; 604/65, 66, 67; 177/50, 245

(56) References Cited

U.S. PATENT DOCUMENTS

| | | | | | |
|---|---|---|---|---|---|
| 3,698,494 | A | * | 10/1972 | Gaudin | 177/118 |
| 4,394,862 | A | * | 7/1983 | Shim | 604/67 |
| 4,469,480 | A | * | 9/1984 | Figlet et al. | 604/52 |
| 4,598,733 | A | * | 7/1986 | Kanno et al. | 137/406 |
| 5,010,968 | A | * | 4/1991 | Barrow | 177/118 |
| 5,371,329 | A | * | 12/1994 | Fillaud | 177/245 |

OTHER PUBLICATIONS

Jennifer M. Burstain et al., Blood Volume Determination as a Function of Hematocrit and Mass in Three Preservative Solutions and Saline, pp. 812–814, 1994.*

COBE CMS Bracket for CMS VRB–1200, COBE catalog, pp. 46–47 date unknown.*

* cited by examiner

Primary Examiner—Jewell V. Thompson

(57) ABSTRACT

An accurate real-time volume measurement of the blood content of a soft-shell venous reservoir is obtained by computing the volume from the weight of the blood in the reservoir modified by the hematocrit of the blood.

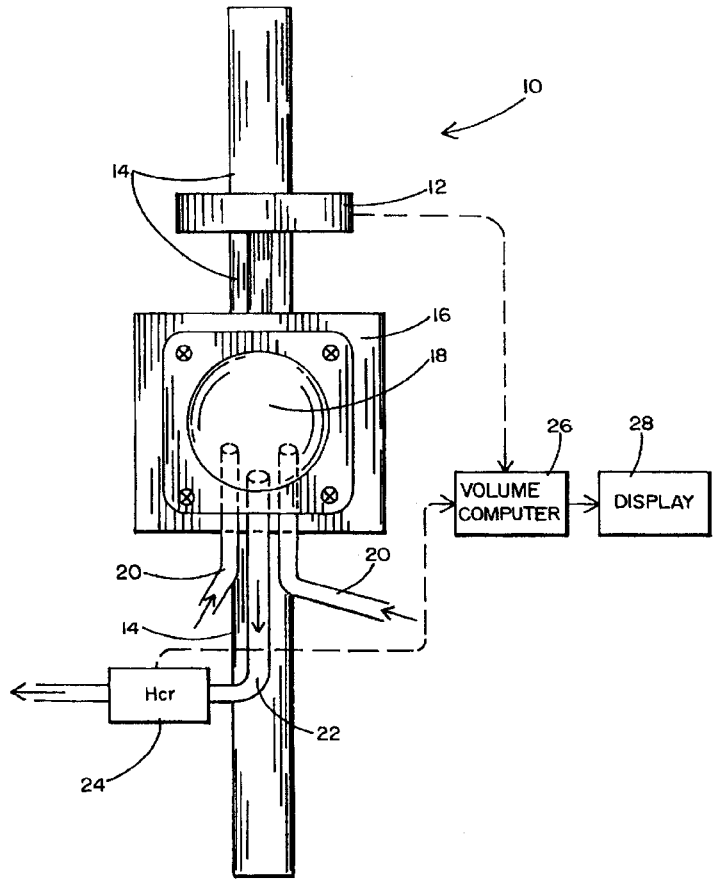

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–4 are cancelled.

Claim 5 is determined to be patentable as amended.

Claim 6, dependent on an amended claim, is determined to be patentable.

New claims 7 and 8 are added and determined to be patentable.

5. [The] *A* system [of claim 3, further] *for measuring the blood volume in a soft-shell venous reservoir,* comprising:
   a) a scale;
   b) a soft-shell blood reservoir suspended from said scale;
   c) a hematocrit sensor so positioned as to sense the hematocrit of the blood in said reservoir;
   d) said scale and sensor being arranged to produce first and second signals representative, respectively, of the net weight of the contents of said reservoir and of said hematocrit;
   e) computing apparatus receiving said first and second signals and computing therefrom an indication of the volume of blood in said reservoir;
   f) display apparatus connected to said computing apparatus and arranged to display said computed volume;
   g) *an outlet conduit arranged to convey blood pumped out of said reservoir; and*
   h) *a fixed support, said conduit being clamped to said support, with a slack portion of said outlet conduit between the clamping point and said reservoir, so as to damp the transmission of cyclical pumping vibrations to said reservoir.*

*7. A method of providing a continuous readout of the blood volume in a soft-shell venous reservoir of a heart-lung machine during cardiac surgery, comprising the steps of:*
   *a) providing a heart-lung machine including a soft-shell venous reservoir;*
   *b) causing blood to flow into and out of said reservoir;*
   *c) continuously sensing in real time the hematocrit of said blood;*
   *d) continuously weighing said reservoir;*
   *e) continuously computing the volume of blood in said reservoir as a function of the weight of said reservoir and said sensed hematocrit; and*
   *f) continuously displaying the volume of blood so computed.*

*8. A system for continuously measuring the blood volume in a soft-shell venous reservoir of a heart-lung machine, comprising:*
   *a) a scale;*
   *b) a soft-shell blood reservoir so associated with said scale as to be weighed thereby;*
   *c) a hematocrit sensor so positioned as to continuously in real time sense the hematocrit of the blood in said reservoir;*
   *d) said scale and sensor being arranged to produce first and second signals representative, respectively, of the net weight of the contents of said reservoir and of said hematocrit;*
   *e) computing apparatus receiving said first and second signals and continuously computing therefrom an indication of the volume of blood in said reservoir; and display apparatus connected to said computing apparatus and arranged to display said computed volume.*

* * * * *